US012667693B2

(12) United States Patent
Markham et al.

(10) Patent No.: US 12,667,693 B2
(45) Date of Patent: Jun. 30, 2026

(54) THERAPEUTIC TREATMENT DEVICE WITH BRAIDED MICROVALVE OCCLUDER

(71) Applicant: TriSalus Life Sciences, Inc., Westminster, CO (US)

(72) Inventors: Michael Brick Markham, Boulder, CO (US); Erik Dean Olson, Castle Rock, CO (US); David Benjamin Jaroch, Arvada, CO (US)

(73) Assignee: TriSalus Life Sciences, Inc., Westminster, CO (US)

( * ) Notice: Subject to any disclaimer, the term of this patent is extended or adjusted under 35 U.S.C. 154(b) by 684 days.

(21) Appl. No.: 17/969,506

(22) Filed: Oct. 19, 2022

(65) Prior Publication Data

US 2024/0131301 A1 Apr. 25, 2024
US 2024/0238558 A9 Jul. 18, 2024

(51) Int. Cl.
*A61M 25/00* (2006.01)

(52) U.S. Cl.
CPC .... *A61M 25/0068* (2013.01); *A61M 25/0075* (2013.01); *A61M 2025/0073* (2013.01);
(Continued)

(58) Field of Classification Search
CPC .......... A61M 25/0068; A61M 25/0075; A61M 2025/0073; A61M 2205/0216;
(Continued)

(56) References Cited

U.S. PATENT DOCUMENTS 4,261,341 A 4/1981 Hakim
4,311,587 A 1/1982 Nose
(Continued)

FOREIGN PATENT DOCUMENTS

CN 101449987 6/2009
CN 103260547 8/2013
(Continued)

OTHER PUBLICATIONS

US 7,169,126 B2, 01/2007, Zadno-Azizi (withdrawn)
(Continued)

*Primary Examiner* — Theodore J Stigell
(74) *Attorney, Agent, or Firm* — Wan Chieh Lee; Haug Partners LLP

(57) ABSTRACT
A vascular treatment device for use in a vessel includes a catheter and a microvalve occluder. The occluder includes braided elastic strands, each with a proximal portion, a central portion, and a distal portion, that are fixed to the outer surface of the catheter. The elastic strands. In an embodiment, the distal portions are attached circumferentially about an outer surface of the catheter at a location toward the distal end of the catheter, the central portions extend proximal and radially outward from the distal end, and the proximal portions of the strands are inverted back radially within the central portions are and coupled circumferentially about the outer surface of the catheter at a location proximally displaced from the distal portions. The proximal portion of the microvalve is coated in a fluid-impermeable membrane, and the distal portions of the strands are substantially uncoated.

21 Claims, 2 Drawing Sheets

(52) U.S. Cl.
CPC .............. *A61M 2205/0216* (2013.01); *A61M 2205/0238* (2013.01); *A61M 2205/0266* (2013.01)

(58) Field of Classification Search
CPC .. A61M 2205/0238; A61M 2205/0266; A61M 2025/0076; A61M 2025/1052; A61M 25/0082; A61M 2025/0042; A61B 17/1204; A61B 17/12109; A61B 17/12172; A61B 17/12177; A61B 2017/00867; A61B 2017/00955; A61B 2017/1205; A61B 2090/3966; A61F 2250/0067; A61F 2/013
See application file for complete search history.

(56) References Cited

U.S. PATENT DOCUMENTS

| | | | |
|---|---|---|---|
| 4,323,525 | A | 4/1982 | Bomat |
| 4,475,972 | A | 10/1984 | Wong |
| 4,655,771 | A | 4/1987 | Wallsten |
| 4,714,460 | A | 12/1987 | Calderon |
| 4,738,740 | A | 4/1988 | Pinchuk et al. |
| 4,800,016 | A | 1/1989 | Yang |
| 4,840,542 | A | 6/1989 | Abbott |
| 4,883,459 | A | 11/1989 | Calderon |
| 4,892,518 | A | 1/1990 | Cupp et al. |
| 5,024,688 | A | 6/1991 | Peter et al. |
| 5,030,199 | A | 7/1991 | Barwick |
| 5,071,407 | A | 12/1991 | Termin |
| 5,084,015 | A | 1/1992 | Moriuchi |
| 5,171,299 | A | 12/1992 | Heitzmann et al. |
| 5,234,425 | A | 8/1993 | Fogarty |
| 5,344,494 | A | 9/1994 | Davidson et al. |
| 5,397,307 | A | 3/1995 | Goodin |
| 5,397,308 | A | 3/1995 | Ellis et al. |
| 5,411,478 | A | 5/1995 | Stillabower |
| 5,419,763 | A | 5/1995 | Hildebrand |
| 5,484,399 | A | 1/1996 | DiResta et al. |
| 5,484,412 | A | 1/1996 | Pierpont |
| 5,496,277 | A | 3/1996 | Termin |
| 5,607,466 | A | 3/1997 | Imbert |
| 5,668,237 | A | 9/1997 | Popall et al. |
| 5,688,237 | A | 11/1997 | Rozga et al. |
| 5,725,571 | A | 3/1998 | Imbert |
| 5,755,687 | A | 5/1998 | Donlon |
| 5,755,769 | A | 5/1998 | Richard |
| 5,759,205 | A | 6/1998 | Valentini |
| 5,810,789 | A | 9/1998 | Powers et al. |
| 5,836,905 | A | 11/1998 | Lemelson |
| 5,836,967 | A | 11/1998 | Schneider |
| 5,893,869 | A | 4/1999 | Barnhart |
| 5,895,399 | A | 4/1999 | Barbut |
| 5,897,567 | A | 4/1999 | Ressemann |
| 5,910,154 | A | 6/1999 | Tsugita |
| 5,911,734 | A | 6/1999 | Tsugita |
| 5,954,745 | A | 9/1999 | Gertler et al. |
| 5,957,974 | A | 9/1999 | Thompson |
| 5,989,281 | A | 11/1999 | Barbut et al. |
| 6,001,118 | A | 12/1999 | Daniel |
| 6,010,522 | A | 1/2000 | Barbut |
| 6,027,520 | A | 2/2000 | Tsugita |
| 6,042,598 | A | 3/2000 | Tsugita |
| 6,051,014 | A | 4/2000 | Jang |
| 6,059,745 | A | 5/2000 | Gelbfish |
| 6,152,946 | A | 11/2000 | Broome |
| 6,165,199 | A | 12/2000 | Barbut |
| 6,165,200 | A | 12/2000 | Tsugita |
| 6,168,579 | B1 | 1/2001 | Tsugita |
| 6,179,851 | B1 | 1/2001 | Barbut |
| 6,231,551 | B1 | 5/2001 | Barbut |
| 6,235,044 | B1 | 5/2001 | Root |
| 6,258,120 | B1 | 7/2001 | Mckenzie |
| 6,306,074 | B1 | 10/2001 | Waksman |
| 6,306,163 | B1 | 10/2001 | Fitz |

| | | | |
|---|---|---|---|
| 6,309,399 | B1 | 10/2001 | Barbut |
| 6,361,545 | B1 | 3/2002 | Macoviak |
| 6,364,895 | B1 | 4/2002 | Greenhalgh |
| 6,371,969 | B1 | 4/2002 | Tsugita |
| 6,371,971 | B1 | 4/2002 | Tsugita |
| 6,375,670 | B1 | 4/2002 | Greenhalgh |
| 6,383,206 | B1 | 5/2002 | Gillick |
| 6,395,014 | B1 | 5/2002 | Macoviak |
| 6,416,495 | B1 | 7/2002 | Kriesel |
| 6,436,112 | B2 | 8/2002 | Wensel |
| 6,443,926 | B1 | 9/2002 | Kletschka |
| 6,478,783 | B1 | 11/2002 | Moorehead |
| 6,485,456 | B1 | 11/2002 | Kletschka |
| 6,485,502 | B2 | 11/2002 | Don Michael |
| 6,499,487 | B1 | 12/2002 | Mckenzie |
| 6,500,203 | B1 | 12/2002 | Thompson |
| 6,520,183 | B2 | 2/2003 | Amar |
| 6,530,935 | B2 | 3/2003 | Wensel |
| 6,533,800 | B1 | 3/2003 | Barbut |
| 6,537,294 | B1 | 3/2003 | Boyle |
| 6,537,297 | B2 | 3/2003 | Tsugita |
| 6,540,722 | B1 | 4/2003 | Boyle |
| 6,551,303 | B1 | 4/2003 | Van Tassel |
| 6,565,552 | B1 | 5/2003 | Barbut |
| 6,569,146 | B1 | 5/2003 | Werner |
| 6,582,396 | B1 | 6/2003 | Parodi |
| 6,589,264 | B1 | 7/2003 | Barbut |
| 6,592,546 | B1 | 7/2003 | Barbut |
| 6,607,506 | B2 | 8/2003 | Kletschka |
| 6,620,148 | B1 | 9/2003 | Tsugita |
| 6,635,070 | B2 | 10/2003 | Leeflang |
| 6,641,553 | B1 | 11/2003 | Chee |
| 6,641,572 | B2 | 11/2003 | Cherkassky |
| 6,645,220 | B1 | 11/2003 | Huter |
| 6,645,222 | B1 | 11/2003 | Parodi |
| 6,645,223 | B2 | 11/2003 | Boyle |
| 6,652,555 | B1 | 11/2003 | Vantassel |
| 6,652,556 | B1 | 11/2003 | Vantassel |
| 6,656,351 | B2 | 12/2003 | Boyle |
| 6,673,090 | B2 | 1/2004 | Root |
| 6,676,682 | B1 | 1/2004 | Tsugita |
| 6,689,150 | B1 | 2/2004 | Vantassel |
| 6,692,508 | B2 | 2/2004 | Wensel |
| 6,692,509 | B2 | 2/2004 | Wensel |
| 6,692,513 | B2 | 2/2004 | Streeter |
| 6,695,813 | B1 | 2/2004 | Boyle |
| 6,695,858 | B1 | 2/2004 | Dubrul |
| 6,699,231 | B1 | 3/2004 | Sterman et al. |
| 6,702,834 | B1 | 3/2004 | Boylan |
| 6,706,053 | B1 | 3/2004 | Boylan |
| 6,706,055 | B2 | 3/2004 | Douk |
| 6,730,108 | B2 | 5/2004 | Vantassel |
| 6,743,196 | B2 | 6/2004 | Barbut et al. |
| 6,746,469 | B2 | 6/2004 | Mouw |
| 6,746,489 | B2 | 6/2004 | Dua |
| 6,802,317 | B2 | 10/2004 | Goebel |
| 6,818,006 | B2 | 11/2004 | Douk |
| 6,830,579 | B2 | 12/2004 | Barbut |
| 6,837,898 | B2 | 1/2005 | Boyle |
| 6,855,154 | B2 | 2/2005 | Abdel-Gawwad |
| 6,866,677 | B2 | 3/2005 | Douk |
| 6,887,258 | B2 | 5/2005 | Denison |
| 6,896,690 | B1 | 5/2005 | Lambrecht |
| 6,902,540 | B2 | 6/2005 | Dorros |
| 6,908,474 | B2 | 6/2005 | Hogendijk |
| 6,911,036 | B2 | 6/2005 | Douk |
| 6,936,060 | B2 | 8/2005 | Hogendijk |
| 6,939,362 | B2 | 9/2005 | Boyle |
| 6,958,059 | B2 | 10/2005 | Zadno-Azizi |
| 6,964,670 | B1 | 11/2005 | Shah |
| 6,964,673 | B2 | 11/2005 | Tsugita |
| 6,974,469 | B2 | 12/2005 | Broome |
| 6,989,027 | B2 | 1/2006 | Allen |
| 6,997,898 | B2 | 2/2006 | Forman |
| 7,044,958 | B2 | 5/2006 | Douk |
| 7,044,966 | B2 | 5/2006 | Svanidze |
| 7,066,946 | B2 | 6/2006 | Douk |
| 7,101,396 | B2 | 9/2006 | Artof |
| 7,108,716 | B2 | 9/2006 | Burnside et al. |

(56)  References Cited

U.S. PATENT DOCUMENTS

| | | |
|---|---|---|
| 7,118,600 B2 | 10/2006 | Dua |
| 7,162,303 B2 | 1/2007 | Levin |
| 7,169,164 B2 | 1/2007 | Borillo |
| 7,172,614 B2 | 2/2007 | Boyle |
| 7,172,621 B2 | 2/2007 | Theron |
| 7,214,237 B2 | 5/2007 | Don Michael |
| 7,217,255 B2 | 5/2007 | Boyle |
| 7,223,253 B2 | 5/2007 | Hogendijk |
| 7,232,452 B2 | 6/2007 | Adams |
| 7,232,453 B2 | 6/2007 | Shimon |
| 7,241,304 B2 | 7/2007 | Boyle |
| 7,250,041 B2 | 7/2007 | Chiu |
| 7,252,675 B2 | 8/2007 | Denison |
| 7,279,000 B2 | 10/2007 | Cartier |
| 7,306,575 B2 | 12/2007 | Barbut |
| 7,322,957 B2 | 1/2008 | Kletschka |
| 7,326,226 B2 | 2/2008 | Root |
| 7,331,973 B2 | 2/2008 | Gesswein |
| 7,338,510 B2 | 3/2008 | Boylan |
| 7,344,549 B2 | 3/2008 | Boyle |
| 7,364,566 B2 | 4/2008 | Elkins |
| 7,371,249 B2 | 5/2008 | Douk |
| 7,425,215 B2 | 9/2008 | Boyle |
| 7,503,904 B2 | 3/2009 | Choi |
| 7,537,600 B2 | 5/2009 | Eskuri |
| 7,544,202 B2 | 6/2009 | Cartier |
| 7,572,272 B2 | 8/2009 | Denison |
| 7,582,100 B2 | 9/2009 | Johnson |
| 7,585,309 B2 | 9/2009 | Larson |
| 7,591,832 B2 | 9/2009 | Eversull |
| 7,604,650 B2 | 10/2009 | Bergheim |
| 7,647,115 B2 | 1/2010 | Levin |
| 7,653,438 B2 | 1/2010 | Deem |
| 7,658,747 B2 | 2/2010 | Forde |
| 7,686,781 B2 | 3/2010 | Vinten-Johansen |
| 7,736,385 B2 | 6/2010 | Agnew |
| 7,780,696 B2 | 8/2010 | Daniel et al. |
| 7,833,242 B2 | 11/2010 | Gilson |
| 7,842,084 B2 | 11/2010 | Bicer |
| 7,846,139 B2 | 12/2010 | Zinn et al. |
| 7,853,333 B2 | 12/2010 | Demarais |
| 7,871,419 B2 | 1/2011 | Devellian et al. |
| 7,873,417 B2 | 1/2011 | Demarais |
| 7,922,691 B2 | 4/2011 | Kletchka |
| 7,935,075 B2 | 5/2011 | Tockman |
| 7,937,143 B2 | 5/2011 | Demarais |
| 7,938,799 B2 | 5/2011 | Epstein |
| 7,955,343 B2 | 6/2011 | Makower |
| 7,993,324 B2 | 8/2011 | Barbut |
| 8,162,879 B2 | 4/2012 | Hattangadi |
| 8,172,792 B2 | 5/2012 | Wang |
| 8,182,446 B2 | 5/2012 | Schaeffer |
| 8,200,312 B2 | 6/2012 | Degani |
| 8,251,948 B2 | 8/2012 | Goldman |
| 8,257,384 B2 | 9/2012 | Bates |
| 8,262,611 B2 | 9/2012 | Teesllink |
| 8,397,578 B2 | 3/2013 | Miesel et al. |
| 8,409,166 B2 | 4/2013 | Wiener |
| 8,500,775 B2 | 8/2013 | Chomas |
| 8,696,698 B2 | 4/2014 | Chomas |
| 8,696,699 B2 | 4/2014 | Chomas |
| 8,821,476 B2 | 9/2014 | Agah |
| 8,852,207 B2 | 10/2014 | Simpson |
| 8,945,116 B2 | 2/2015 | Macadam et al. |
| 8,951,280 B2 | 2/2015 | Cohn et al. |
| 9,023,010 B2 | 5/2015 | Chiu |
| 9,061,117 B2 | 6/2015 | Roberts |
| 9,078,982 B2 | 7/2015 | Lane |
| 9,084,857 B2 | 7/2015 | Cully et al. |
| 9,089,341 B2 | 7/2015 | Chomas |
| 9,089,668 B2 | 7/2015 | Chomas et al. |
| 9,107,734 B2 | 8/2015 | Belson |
| 9,126,016 B2 | 9/2015 | Chomas |
| 9,174,020 B2 | 11/2015 | Allen |
| 9,205,226 B2 | 12/2015 | Allen |
| 9,265,914 B2 | 2/2016 | Fulton, III |
| 9,295,540 B2 | 3/2016 | Chomas |
| 9,345,499 B2 | 5/2016 | Strauss |
| 9,364,358 B2 | 6/2016 | Cohen |
| 9,457,171 B2 | 10/2016 | Agah |
| 9,463,304 B2 | 10/2016 | Agah |
| 9,474,533 B2 | 10/2016 | Mathis et al. |
| 9,539,081 B2 | 1/2017 | Chomas |
| 9,550,046 B1 | 1/2017 | Allen |
| 9,597,480 B2 | 3/2017 | Purdy |
| 9,604,037 B2 | 3/2017 | Fischer, Jr. |
| 9,629,721 B2 | 4/2017 | Mckinnis |
| 9,737,693 B2 | 8/2017 | Helkowski |
| 9,770,319 B2 | 9/2017 | Pinchuk |
| 9,808,332 B2 | 11/2017 | Chomas |
| 9,844,383 B2 | 12/2017 | Allen |
| 9,913,959 B2 | 3/2018 | Purdy |
| 9,968,740 B2 | 5/2018 | Pinchuk |
| 10,076,404 B2 | 9/2018 | Bonnette |
| 10,092,742 B2 | 10/2018 | Genstler |
| 10,099,040 B2 | 10/2018 | Agah |
| 10,130,762 B2 | 11/2018 | Allen |
| 10,307,241 B2 | 6/2019 | Zhang |
| 10,350,382 B1 | 7/2019 | Halstead |
| 10,588,636 B2 | 3/2020 | Pinchuk |
| 10,780,250 B1 | 9/2020 | Arepally et al. |
| 10,813,739 B2 | 10/2020 | Chomas |
| 11,090,460 B2 | 8/2021 | Jaroch et al. |
| 11,090,486 B2 | 8/2021 | Chappa et al. |
| 11,324,619 B1 | 5/2022 | Yacoby et al. |
| 11,400,263 B1 | 8/2022 | Arepally et al. |
| 2001/0016755 A1 | 8/2001 | Addis |
| 2001/0041862 A1 | 11/2001 | Glickman |
| 2002/0042593 A1 | 4/2002 | Mickley |
| 2002/0049468 A1 | 4/2002 | Streeter et al. |
| 2002/0091408 A1 | 7/2002 | Sutton et al. |
| 2002/0161390 A1 | 10/2002 | Mouw |
| 2002/0161394 A1 | 10/2002 | Macoviak |
| 2003/0078614 A1 | 4/2003 | Salahich et al. |
| 2003/0097114 A1 | 5/2003 | Ouriel |
| 2003/0125790 A1 | 7/2003 | Fastovsky |
| 2003/0176884 A1 | 9/2003 | Berrada et al. |
| 2003/0181943 A1 | 9/2003 | Daniel et al. |
| 2003/0187474 A1 | 10/2003 | Keegan |
| 2003/0212361 A1 | 11/2003 | Boyle |
| 2003/0233115 A1 | 12/2003 | Eversull |
| 2004/0006305 A1 | 1/2004 | Hebert |
| 2004/0054315 A1 | 3/2004 | Levin |
| 2004/0068288 A1 | 4/2004 | Palmer |
| 2004/0143185 A1 | 7/2004 | Zatezalo |
| 2004/0215142 A1 | 10/2004 | Matheis |
| 2004/0220511 A1 | 11/2004 | Scott |
| 2004/0220521 A1 | 11/2004 | Barbut |
| 2004/0220609 A1 | 11/2004 | Douk |
| 2004/0225354 A1 | 11/2004 | Allen |
| 2004/0256584 A1 | 12/2004 | Zimmerling |
| 2004/0260333 A1 | 12/2004 | Dubral |
| 2005/0004517 A1 | 1/2005 | Courtney |
| 2005/0010285 A1 | 1/2005 | Lambrecht |
| 2005/0015048 A1 | 1/2005 | Chiu |
| 2005/0015112 A1 | 1/2005 | Cohn |
| 2005/0043678 A1 | 2/2005 | Freyman |
| 2005/0113798 A1 | 5/2005 | Slater et al. |
| 2005/0119688 A1 | 6/2005 | Burgheim |
| 2005/0149112 A1 | 7/2005 | Barbut |
| 2005/0261759 A1 | 11/2005 | Lambrecht |
| 2006/0015136 A1 | 1/2006 | Besselink |
| 2006/0124140 A1 | 6/2006 | Forsell |
| 2006/0167537 A1 | 7/2006 | Larsson |
| 2006/0173490 A1 | 8/2006 | Lafontaine |
| 2006/0177478 A1 | 8/2006 | Humes |
| 2006/0229645 A1 | 10/2006 | Bonnette et al. |
| 2006/0263301 A1 | 11/2006 | Vernon |
| 2006/0264898 A1 | 11/2006 | Beasley et al. |
| 2007/0106258 A1 | 5/2007 | Chiu et al. |
| 2007/0106324 A1 | 5/2007 | Gamer |
| 2007/0112371 A1 | 5/2007 | Cangialosi |
| 2007/0179590 A1 | 8/2007 | Lu |
| 2007/0239135 A9 | 10/2007 | Barbut |

(56) References Cited

U.S. PATENT DOCUMENTS

| | | |
|---|---|---|
| 2007/0282436 A1 | 12/2007 | Pinchuk |
| 2008/0031740 A1 | 2/2008 | Miyazaki |
| 2008/0031962 A1 | 2/2008 | Boyan |
| 2008/0033341 A1 | 2/2008 | Grad |
| 2008/0038313 A1 | 2/2008 | Addis et al. |
| 2008/0039786 A1 | 2/2008 | Epstein |
| 2008/0051758 A1 | 2/2008 | Rioux |
| 2008/0097273 A1 | 4/2008 | Levin |
| 2008/0103523 A1 | 5/2008 | Chiu |
| 2008/0147007 A1 | 6/2008 | Freyman |
| 2008/0234796 A1 | 9/2008 | Dorn |
| 2009/0018486 A1 | 1/2009 | Goren et al. |
| 2009/0018498 A1 | 1/2009 | Chiu |
| 2009/0076409 A1 | 3/2009 | Wu |
| 2009/0088676 A1 | 4/2009 | Murata |
| 2009/0198321 A1 | 8/2009 | Sutermeister |
| 2009/0222035 A1 | 9/2009 | Schneiderman |
| 2009/0234266 A1 | 9/2009 | Solomon |
| 2009/0234283 A1 | 9/2009 | Burton |
| 2009/0264819 A1 | 10/2009 | Diethrich |
| 2010/0168785 A1 | 7/2010 | Parker |
| 2010/0274277 A1 | 10/2010 | Eaton |
| 2010/0331815 A1 | 12/2010 | Alt |
| 2011/0046542 A1 | 2/2011 | Evans |
| 2011/0130657 A1 | 6/2011 | Chomas |
| 2011/0137331 A1 | 6/2011 | Walsh et al. |
| 2011/0137399 A1 | 6/2011 | Chomas |
| 2011/0218494 A1 | 9/2011 | Gerrans |
| 2011/0288529 A1 | 11/2011 | Fulton |
| 2011/0295114 A1 | 12/2011 | Agah |
| 2011/0295203 A1 | 12/2011 | Hayes |
| 2012/0116351 A1 | 5/2012 | Chomas |
| 2012/0259206 A1 | 10/2012 | Roberts |
| 2013/0079731 A1 | 3/2013 | Chomas |
| 2013/0110041 A1 | 5/2013 | Farag |
| 2013/0116655 A1 | 5/2013 | Bacino |
| 2013/0226166 A1 | 8/2013 | Chomas |
| 2014/0039544 A1 | 2/2014 | Bergheim |
| 2014/0066830 A1 | 3/2014 | Lad |
| 2014/0073536 A1 | 3/2014 | Lin et al. |
| 2014/0207178 A1 | 7/2014 | Chomas |
| 2014/0276135 A1 | 9/2014 | Agah |
| 2014/0276411 A1 | 9/2014 | Cowan et al. |
| 2014/0364835 A1 | 12/2014 | Allen |
| 2014/0378951 A1 | 12/2014 | Dye |
| 2015/0272716 A1 | 10/2015 | Pinchuk |
| 2015/0306311 A1 | 10/2015 | Pinchuk |
| 2016/0015948 A1 | 1/2016 | Agah |
| 2016/0074633 A1 | 3/2016 | Schaffner |
| 2016/0082178 A1 | 3/2016 | Agah |
| 2016/0235942 A1 | 8/2016 | Alt |
| 2016/0235950 A1 | 8/2016 | Murata |
| 2016/0249969 A1 | 9/2016 | Santoinanni et al. |
| 2016/0256626 A9 | 9/2016 | Chomas |
| 2016/0310148 A1 | 10/2016 | Allen |
| 2017/0000493 A1 | 1/2017 | Boehm, Jr. |
| 2017/0049946 A1 | 2/2017 | Kapur |
| 2017/0056629 A1 | 3/2017 | Agah |
| 2017/0157370 A1 | 6/2017 | Agah et al. |
| 2017/0173309 A1 | 6/2017 | Fischer, Jr. |
| 2017/0189654 A1 | 7/2017 | Schwartz et al. |
| 2017/0209666 A1 | 7/2017 | Quigley |
| 2017/0319820 A1 | 11/2017 | Johnson |
| 2017/0368306 A1 | 12/2017 | Tal |
| 2018/0055620 A1 | 3/2018 | Chomas |
| 2018/0116522 A1 | 5/2018 | Brenneman |
| 2018/0125502 A1 | 5/2018 | Allen |
| 2018/0250469 A1 | 9/2018 | Pinchuk |
| 2018/0263752 A1* | 9/2018 | Pinchuk ................. A61F 2/0108 |
| 2018/0289464 A1 | 10/2018 | Kassab |
| 2018/0304054 A1* | 10/2018 | McCleary ............... A61L 29/06 |
| 2018/0333563 A1 | 11/2018 | Agah |
| 2019/0046157 A1 | 2/2019 | Unser |
| 2019/0083705 A1 | 3/2019 | Allen |
| 2020/0038586 A1 | 2/2020 | Chomas et al. |
| 2020/0078555 A1 | 3/2020 | Agah et al. |
| 2020/0108239 A1 | 4/2020 | Arepally et al. |
| 2020/0178976 A1 | 6/2020 | Pinchuk |
| 2020/0205840 A1 | 7/2020 | Adawi et al. |
| 2020/0261695 A1 | 8/2020 | Jaroch et al. |
| 2020/0297351 A1 | 9/2020 | Allen |
| 2020/0383688 A1 | 12/2020 | Olson et al. |
| 2021/0007754 A1* | 1/2021 | Milhous ........... A61B 17/12145 |
| 2021/0244473 A1 | 8/2021 | Cook et al. |

FOREIGN PATENT DOCUMENTS

| | | |
|---|---|---|
| CN | 203107204 | 8/2013 |
| CN | 105007973 | 10/2015 |
| CN | 105208946 | 12/2015 |
| DE | 8910603 U1 | 12/1989 |
| EP | 0416662 B1 | 3/1991 |
| EP | 0533511 A1 | 3/1993 |
| EP | 0554579 A1 | 8/1993 |
| EP | 1226795 | 7/2002 |
| EP | 1527740 | 5/2005 |
| EP | 1743524 A1 | 1/2007 |
| EP | 1803423 | 7/2007 |
| EP | 2359893 | 8/2011 |
| EP | 3458136 | 3/2019 |
| FR | 2652267 A1 | 3/1991 |
| GB | 2020557 B | 11/1979 |
| JP | 2006051144 A | 2/2006 |
| JP | 2006523515 | 10/2006 |
| WO | 8905667 | 6/1989 |
| WO | 9902093 A1 | 1/1999 |
| WO | 199916382 | 4/1999 |
| WO | WO-1999023976 | 5/1999 |
| WO | WO-1999042059 | 8/1999 |
| WO | 199944510 A1 | 9/1999 |
| WO | 200141679 | 6/2001 |
| WO | 200145592 | 6/2001 |
| WO | 200149215 A2 | 7/2001 |
| WO | 0197879 | 12/2001 |
| WO | 02055146 A1 | 7/2002 |
| WO | 2004043293 | 5/2004 |
| WO | WO-2004075776 | 9/2004 |
| WO | 2007084431 | 7/2007 |
| WO | 2011068924 | 6/2011 |
| WO | WO-2011079111 | 6/2011 |
| WO | WO-2015015314 | 2/2015 |
| WO | WO-2016149653 | 9/2016 |
| WO | WO-2016178177 | 11/2016 |
| WO | WO-2019140381 | 7/2019 |

OTHER PUBLICATIONS

Allogenic Chimeric Antigen Receptor-Modified Cells for Adoptive Cell Therapy of Cancer, Marcus, Assaf et al., Mar. 24, 2014, Expert Opinion of Biological Therapy, vol. 14, Issue 7.

A Study of the Geometrical and Mechanical Properties of a Self-Expandig Metallic Stent Theory and Experiment, Dr. Michael R. Jedwab, Claude 0. Clerc, Journal of Applied Biomaterials, vol. 4, Issue 1, pp. 77-85, Spring 1993.

U.S. Appl. No. 61/266,068, filed Dec. 2, 2009, Chomas et al.

U.S. Appl. No. 61/382,290, filed Sep. 13, 2010, Chomas et al.

Cannulation of the Cardiac Lymphatic Sytem in Swine, Vazque-Jiminez et al., European Journal of Cardio-thoracic Surgery 18 (2000) 223-232.

Catheter-Based Renal Sympathetic Denervation for Resistant Hypertension: a Multicentre Safety and Proof-of-Principle Cohort Study, Krum et al., The Lancet, 2009.

Development of Repeatable Microcatheter Access Port for Intra-arterial Therapy of Liver Cancer, Yasushi Fukuoka et al., Cardiovasc Intervent Radiol (2019) 42:298-303.

Embolization II, Scientific Session 11, JVIR, Mar. 27, 2012.

Embolization procedure lowers levels of "hunger hormone," leads to weight loss, EurekAlert Public Release, Mar. 7, 2013.

Estimation of Tumor Interstitial Fluid Pressure (TIFP) Noninvasively, Long Lian Liu et al., PLOS One | DOI:10.1371/journal.pone. 0140892 Jul. 28, 2016.

(56)                  References Cited

OTHER PUBLICATIONS

Finite Element Stent Design, M. De Beule, R. Van Impe, P. Verdonck, B. Verhegghe, Computer Methods in Biomechanics and Biomedical Engineering, 2005.
First-In-Man Study of Left Gastric Artery Embolization for Weight Loss, Nicholas Kipshidze et al., ACC.13, E2056, UACC Mar. 12, 2013, vol. 61, Issue 10.
Fusion Drug Delivery System-Novel Catheter/Stent Design for Targeted Drug Delivery, Gerschwind & Barnett, Non-Published US provisional patent application filed Sep. 17, 2007.
International Search Report and Written Opinion of Application No. PCT/US16/23723 dated Sep. 2, 2016.
International Search Report and Written Opinion of Application No. PCT/US19/13482 dated Jun. 10, 2019.
International Search Report of PCT/US18/22171 dated Aug. 3, 2018.
Japanese Office Action dated Apr. 28, 2021 of Application No. 2020-082002.
Left Gastric Embolization Leads to Weight Loss, Bariatriac News, Owen Haskins, Dec. 4, 2013.
Long-Term Catheterization of the Intestinal Lymph Trunk and Collection of Lymph in Neonatal Pigs, Richard R. Uwiera et al., Journal of Visualized Experiments, Mar. 2016, 109, e53457.
Lymphaniography to Treat Postoperative Lymphatic Leakage: A Technical Review, Edward Wolfgang Lee, et al., Korean Journal of Radiology 15(6), Nov./Dec. 2014.
Radiologic Placement of Side-hole Catheter with Tip Fixation for Hepatic Arterial Infusion Chemotherapy, Toshihiro Tanaka et al., J Vasc Interv Radiol 2003: 14:63-68.
Renal Denervation as a Therapeutic Approach for Hypertension: Novel Implications for an Old Concept, Schlaich et al., Hypertension, Journal of the American Heart Association, 2009, 54:1195-1201.
Renal Sympathetic-Nerve Ablation for Uncontrolled Hypertension, Schlaich et al., The New England Journal of Medicine, 2009, pp. 932-934, Aug. 27, 2009.
RenovoCath(tm) RC120 The Future of Targeted Delivery, RenovoRx Inc., web brochure downloaded from Internet on Feb. 2, 2015.
Superselective Retrograde Lymphatic Duct Embolization for Management of Postoperataive Lymphatic Leak, Bulent Arslan et al., Diagn Interv Radiol 2017; 23:379-380.
Chinese Office Action and Search Report dated May 27, 2021 of Patent Application No. 201880033448.X.

Chinese Office Action dated Nov. 29, 2022 of Application No. 202111184263.9.
CN Search Report dated Nov. 17, 2022 of Application No. 202111184263.9.
Japanese Office Action dated Jul. 12, 2022 of Applcation No. 2019-551584.
International Search Report and Written Opinion dated Mar. 13, 2024 issued in international application No. PCT/US2023/035480.
U.S. Appl. No. 17/375,779, Arepally et al.
U.S. Appl. No. 17/671,296, Arepally et al.
Rose et al., Temporary Splenic Artery Balloon Occlusion for Protection of Nonsplenic Vascular Beds During Splenic Emboliza-tion, Technical Innovation, May 1, 1998, pp. 1186-1188.
Rose et al., "Downstream Hepatic Arterial Blood Pressure Changes Caused by Deployment of the Surefire AntiReflux Expandable Tip", Clinical Investigation, Dec. 19, 2012, 8 pages.
Rose et al., "Feasibility of Intraprocedural Transluminal Hepatic and Femoral Artery Blood Pressure Measurements as an Alternative Embolization Safety Endpoint When Antireflux Devices Are Used During Lobar Chemoembolization", Vascular and Interventional Radiology, Technical Innovation, Jun. 23, 2015, pp. 196-202.
Rose et al., "Quantification of Blood Pressure Changes in the Vascular Compartment When Using an Anti-Reflux Catheter during Chemoembolization versus Radioembolization: A Retrospective Case Series", Clinical Study, Nov. 10, 2016, 8 pages.
Rose et al., The Beauty and Bane of Pressure-Directed Embolotherapy: Hemodynamic Principles and Preliminary Clinical Evidence, Dec. 27, 2018.
Search Report and Written Opinion of Application No. PCT/US19/54406 dated Jan. 6, 2020.
Chinese Office Action and Search Report dated Jan. 10, 2022 of Application No. 201980016342.3.
EP Search Report and Written Opinion of Application No. EP19739019 dated Sep. 17, 2021.
Canadian Office Action dated Jun. 3, 2022 of Application No. 3,139,118.
International Search Report and Written Opinion of Application No. PCT/US2020/034626 dated Aug. 26, 2020.
Japanese Office Action dated May 10, 2022 of Application No. JP 2021-572025.
Japanese Office Action dated Dec. 14, 2021 of Application No. JP2019-551584.
Japanese Office Action dated Jul. 12, 2022 of Application No. JP2019-551584.

* cited by examiner

THERAPEUTIC TREATMENT DEVICE WITH BRAIDED MICROVALVE OCCLUDER

CROSS-REFERENCE TO RELATED PATENTS

This application is related to co-owned U.S. Pat. No. 8,696,698, and co-owned U.S. Pat. No. 10,588,636, which are hereby incorporated by reference herein in their entireties.

BACKGROUND OF THE INVENTION

1. Field of Invention

The disclosure relates generally to catheters for delivering a therapeutic treatment into a blood vessel. More particularly, this disclosure relates to catheters having microvalves at the distal end thereof to increase penetration of the therapeutic treatment into targeted blood vessels and reduces reflux of the therapeutic treatment into non-targeted blood vessels.

2. State of the Art

Intravascular therapeutic treatments are often clinically delivered to treat a wide range of diseases. By way of example, intravascular embolization, chemo-embolization, and radio-embolization therapies are used to treat a range of diseases, such as hypervascular liver tumors, uterine fibroids, secondary cancer metastasis in the liver, pre-operative treatment of hypervascular menangiomas in the brain and bronchial artery embolization for hemoptysis.

Non-targeted delivery of various therapies can lead to adverse events and morbidity. In addition, non-targeted delivery suggests that the intended target of the delivery is not receiving the full dose of therapy.

Infusion with a standard infusion microcatheter allows bi-directional flow. That is, the use of a microcatheter to infuse a therapeutic agent allows blood and the infused therapeutic agent to move forward in addition to allowing blood and the therapeutic agent to be pushed backward (reflux). Reflux of a therapeutic agent causes non-target damage to surrounding healthy organs. In interventional oncology therapeutic procedures, the goal is to bombard a cancer tumor with either radiation or chemotherapy. It is important to maintain forward flow throughout the entire vascular tree in the target organ in order to deliver therapies into the distal vasculature, where the therapy can be most effective. This issue is amplified in hypovascular tumors or in patients who have undergone chemotherapy, where slow flow limits the dose of therapeutic agent delivered and reflux of agents to non-target tissue can happen well before the physician has delivered the desired dose.

The pressure in a vessel at multiple locations in the vascular tree changes during a therapeutic infusion procedure. Initially, the pressure is high proximally, and decreases over the length of the vessel. Forward flow of therapy occurs when there is a pressure drop. If there is no pressure drop over a length of vessel, therapy does not flow downstream. If there is a higher pressure at one location, such as at the orifice of a catheter, the therapeutic therapy flows in a direction toward lower pressure. If the pressure generated at the orifice of an infusion catheter is larger than the pressure in the vessel proximal to the catheter orifice, some portion of the infused therapeutic therapy travels up stream (reflux) into non-target vessels and non-target organs. This phenomenon can happen even in vessels with strong forward flow if the infusion pressure (pressure at the orifice of the catheter) is sufficiently high.

In clinical practice with a standard infusion catheter, the physician attempts to infuse the therapeutic agent with pressure that does not cause reflux. In doing this, the physician slows the infusion rate (and infusion pressure) or stops the infusion completely. The clinical impact of current infusion catheters and techniques is two fold: low doses of the therapeutic agent is delivered and there is poor distal penetration into the target vessels.

Additionally, reflux can be a time-sensitive phenomenon. Sometimes, reflux occurs as a response to an injection of the therapeutic agent, where the reflux occurs rapidly (e.g., in the time-scale of milliseconds) in a manner which is too fast for a human operator to respond. Also, reflux can happen momentarily, followed by a temporary resumption of forward flow in the blood vessel, only to be followed by additional reflux.

Various devices have been proposed to increase distal penetration while preventing reflux. For example, co-owned U.S. Pat. No. 8,696,698, which has been incorporated by reference herein, describes a microvalve infusion system for infusing a therapeutic agent that has a dynamically adjustably filter valve coupled at a distal end of a delivery catheter. The delivery catheter and filter valve self-expand when deployed from a delivery catheter. The filter valve is naturally spring biased by its construction of filamentary elements to automatically partially expand within a vessel when it is deployed from the outer catheter, and is coated with a porous polymer coating that has a pore size sufficiently small to filter a therapeutic agent. In view of the construction, upon infusion, an increase in fluid pressure results within the filter valve and causes the filter valve to open, extend across a vessel, and thereby prevent reflux of the infused therapeutic agent. In addition, as the fluid is pressurized through the delivery catheter and into the filter valve, the downstream pressure in the vessel is increased which facilitates maximum uptake into the target tissue for therapeutically delivered agents. Further, the filter valve is responsive to local pressure about the valve which thereby enables substantially unrestricted forward flow of blood in the vessel, and reduces or stops reflux (regurgitation or backward flow) of therapeutic agents which are introduced into the blood.

However, the devices in U.S. Pat. No. 8,696,698 have certain issues that may not always be advantageous for a given situation. The filter valve devices disclosed are generally well-adapted where tracking the occluder into small vessels is not a significant requirement; trackability in tortuous branching vasculature can be limited. The distal end of the device in a collapsed, undeployed state is defined by the size of the deployment catheter, which can be significantly larger than the catheter that supports the filter valve and significantly larger than the outer diameter of a guidewire used to the guide the microvalve to the target location within the vessel. As such, tracking the filter valve into the smaller vascular branches may not be optimal. In addition, once the device is tracked to a treatment location, deployment of the filter valve requires that the frictional force between the filter valve and the outer deployment catheter be overcome.

Co-owned U.S. Pat. No. 10,588,636, previously incorporated herein, described a microvalve infusion system for infusing a therapeutic agent and which addresses device trackability. Referring to Prior Art FIG. 1, the system 10 includes a flexible infusion catheter 12 having a hub 14 at a proximal end 16 and a filter valve occluder 18 coupled to a distal end 20. The filter valve occluder 18 includes elastic strands 22 that each include a proximal portion 24, a central portion 26, and a distal portion 28. The proximal portions 24 are attached circumferentially about at an outer surface 30 of the catheter 12 at a location proximal of a distal orifice 32 of the catheter, the central portions 26 extend radially outward and toward the orifice 32, and the distal portions 28 of the strands are inverted back into the filter valve occluder 18 and coupled circumferentially about the outer surface 30 of the catheter 12. The proximal and central portions 24, 26 of the strands 22 are coated in a polymeric filter coating 34 that extends between and across the strands 18. The distal portions 28 of the strands 22 are uncoated. This microvalve infusion system 10 is commercially produced and sold as the TRINAV® infusion system by Trisalus Life Sciences, Inc., Westminster, CO. In use, the microvalve infusion system can be deployed from an introducer sleeve 36 at a target vessel location; but is not required to be used with an introducer sleeve. Rather, the infusion system can be advanced over a guidewire without any introducer sleeve, providing good results with trackability. Upon introduction in the vessel, the filter valve occluder 18 has been shown to dynamically operate in sync with the cardiac cycle and preserve more than 70 percent of antegrade blood flow in a vessel past the microvalve occluder, while providing intended retrograde blockade of therapeutics. Further, the design permits atraumatically increasing the pressure of therapeutic infusion into local resistive tumor vessels to enable deeper perfusive delivery of therapeutics.

SUMMARY OF THE INVENTION

An infusion device is provided that includes a catheter and a microvalve. The catheter has a proximal end, a distal end, and a lumen extending from the proximal end to the distal end and opening at a distal orifice. The microvalve is coupled to the distal end of the catheter proximal of the orifice.

The microvalve is formed from a naturally spring-biased filamentary construction that is biased to radially expand and has a proximal end and a distal end. The elastic strands of the filamentary construction are formed in a braided mesh. The elastic strands each include a proximal portion, a central portion, and a distal portion. The distal portions are attached circumferentially about at an outer surface of the catheter at a location toward the distal end but proximal of the orifice of the catheter, the central portions extend proximal and radially outward from the distal end, and the proximal portions of the strands are inverted back radially within the central portions, extend distally, and are coupled circumferentially about the outer surface of the catheter at a location proximally displaced from the distal portions of the strands. The proximal and central portions of the strands are coated in a polymeric filter or membrane material that extends between and across the strands to render that area of the microvalve fluid-impermeable, whereas the distal portions of the strands are substantially uncoated in a polymeric filter such that fluid can pass between the open strands.

The shape of the microvalve is axially reversed from known infusion microvalves. This provides several advantages. First, the shape naturally defines a tapered lead end for advancement within the vessel. This tapered shape has significantly lower drag when advancing forward along the vascular wall, thus reducing possibility of vessel spasm. Second the shape provides a large bulbous proximal end with significantly higher resistance to antegrade flow about the flow than prior dynamic microvalve devices. This results in a greater reduction of flow about the valve and a significant pressure drop distal of the valve which has unexpected advantages for various therapeutic delivery procedures. For example, for therapeutic regional delivery to various tumors in an organ, including by way of example in the liver and pancreas, it has been found beneficial to reduce vascular flow into the organ prior to and during pressurized delivery of the therapeutic agent into the organ.

In another embodiment of a microvalve, the distal ends of braided strands are attached circumferentially about at an outer surface of the catheter at a location toward the distal end but proximal of the orifice of the catheter, the central portions of braided strands extend proximal and radially outward from the distal end, and the proximal portions of the braided strands extend radially inward and are coupled circumferentially about the outer surface of the catheter at a location proximally displaced from the distal portions of the braided strands such that the braided strands define a bulb shape. The length between the proximal and distal ends is fixed. The proximal and central portions of the strands are coated in a polymeric filter or membrane material that extends between and across the braided strands to render that area of the microvalve fluid-impermeable, whereas the distal portions of the braided strands are substantially uncoated in a polymeric filter such that fluid can pass between the open braided strands. This construct provides lower flow resistance relative to the tapered lead, bulbous proximal end construction described above, and higher drag when advancing the microvalve in the vessel.

BRIEF DESCRIPTION OF DRAWINGS

Prior art

DETAILED DESCRIPTION OF THE PREFERRED EMBODIMENTS

With reference to the human body and components of the devices and systems described herein which are intended to be hand-operated by a user, the terms "proximal" and "distal" are defined in reference to the user's hand, with the term "proximal" being closer to the user's hand, and the term "distal" being further from the user's hand, unless alternate definitions are specifically provided.

Figures 1, 2:
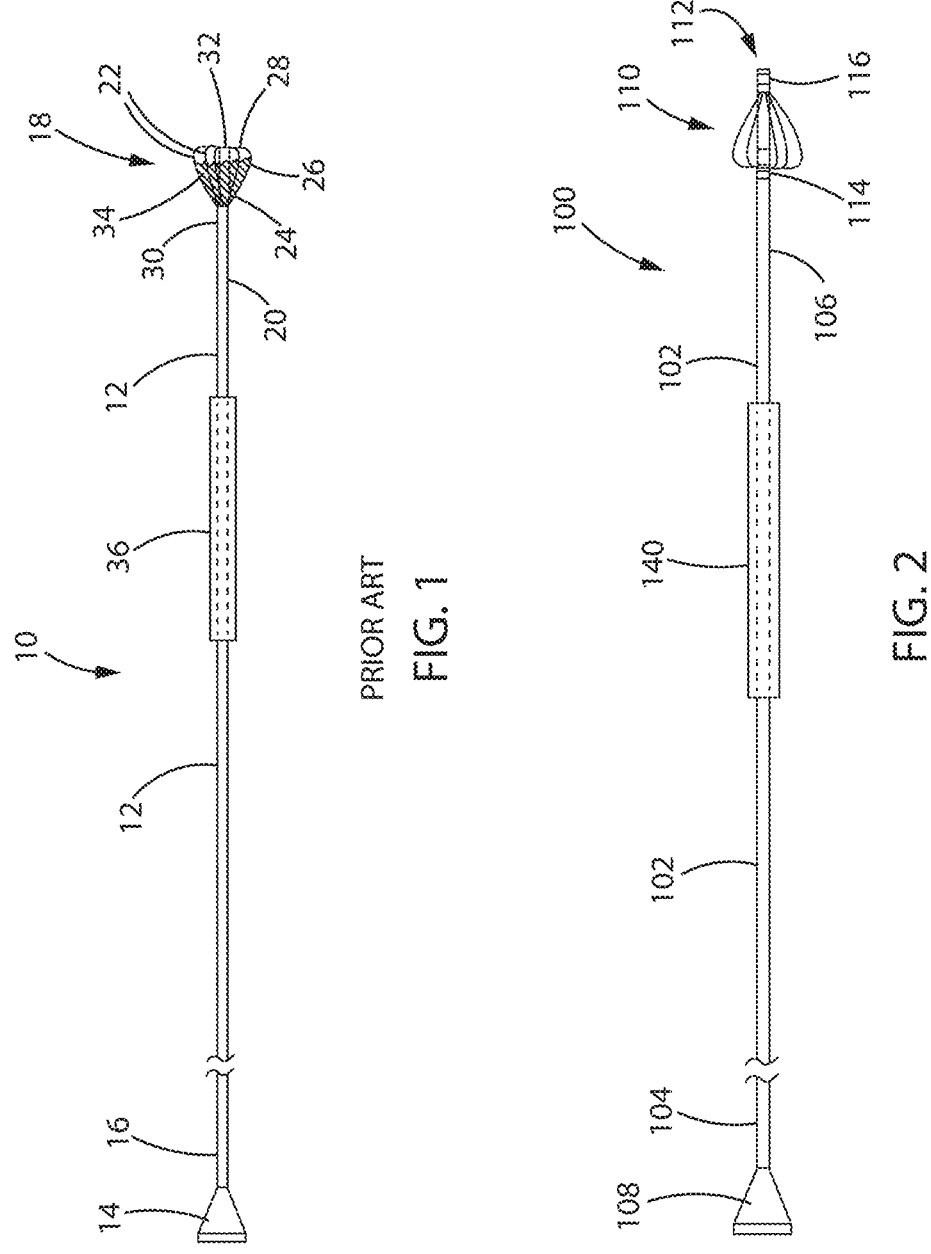
FIG. 1 is a side elevation of a prior art microvalve infusion system.
FIG. 2 is side elevation of a microvalve infusion system according to an embodiment described herein.
Figure 3:
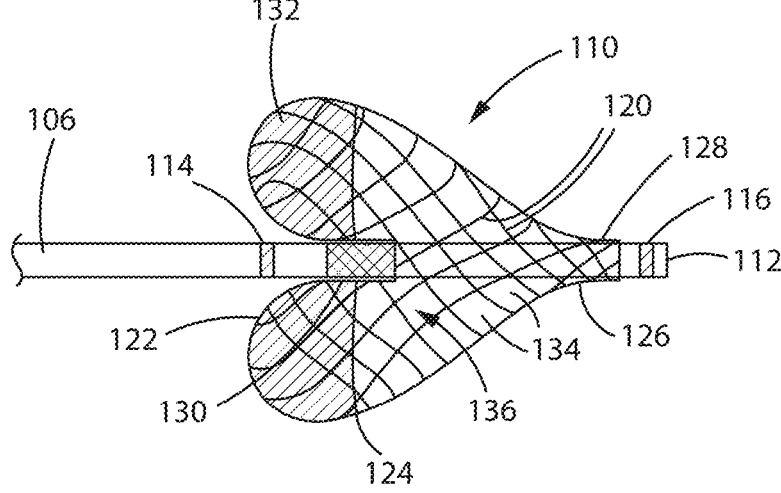
FIG. 3 is an enlarged view of the distal end of the microvalve infusion system shown in FIG. 2.

A first exemplary embodiment of a microvalve device 100 according to the invention is shown in FIGS. 2 and 3. It is noted that respective portions of the system illustrated in such figures are not shown proportional to their intended size, but rather that the distal portion is illustrated significantly enlarged for purposes of explanation. As shown in FIG. 2, the device 100 includes a flexible catheter 102 having a proximal end 104 and a distal end 106, a hub 108 coupled to the proximal end 104 of the catheter, and a filter valve vessel occluder 110, described in more detail below, coupled to the distal end 106 of the catheter 102. An infusion lumen extends from the hub 108 through to the distal end 106 of the catheter 102 and exiting at a distal orifice 112 and is adapted for delivery of a therapeutic agent from outside the body of the patient (not shown) to a target vessel (artery or vein) in the patient. The hub 108 is adapted to facilitate advancement of a guidewire through the infusion lumen and/or coupling of a syringe for infusion of a therapeutic through the infusion lumen. Any hub suitable for at least facilitating delivery of a therapeutic into the infusion lumen can be utilized.

One or more radio-opaque marker bands 114, 116 are provided proximal and/or distal of the vessel occluder 110. During use of the device 100, the in vivo positions of the marker bands 114, 116 viewed fluoroscopically indicates the location of the vessel occluder 114 relative to anatomical landmarks.

The catheter 102 is between two and eight feet long, and has an outer diameter of between 0.67 mm and 3 mm (corresponding to catheter sizes 2 French to 12 French), and is made from a liner made of fluorinated polymer such as polytetrafluoroethylene (PTFE) or fluorinated ethylene propylene (FEP), a braid made of metal such as stainless steel or nickel titanium alloy, or a polymer such as polyethylene terephthalate (PET) or liquid crystal polymer, and an outer coating made of a polyether block amide thermoplastic elastomeric resin such as Pebax®, polyurethane, polyamide, copolymers of polyamide, polyester, copolymers of polyester, fluorinated polymers, such as PTFE, FEP, polyimides, polycarbonate or any other suitable material, or any other standard or specialty material used in making catheters used in the bloodstream.

Turning to FIG. 3, the filter valve occluder 110 is composed of multiple metal (e.g., stainless steel or nickel-titanium alloy) or polymer filaments or strands 120 in a tubular braided construction, which form a substantially closed shape when deployed and not subject to outside forces. Where polymeric filaments are utilized, the filaments 120 may be composed of PET, polyethylene-napthalate (PEN), liquid crystal polymer, fluorinated polymers, nylon, polyamide or any other suitable polymer. If desired, when polymeric filaments are utilized, one or more metal filaments may be utilized in conjunction with the polymeric filaments. According to one aspect of the invention, where a metal filament is utilized, it may be of radio-opaque material to facilitate tracking the filter valve occluder 110 and its configuration within the body. In an expanded diameter configuration, the filter valve occluder 110 is capable of being modified in shape by fluid forces. It is preferred that the filaments 120 not be bonded to each between their ends so to enable the valve to rapidly automatically move in response to dynamic flow conditions. The multiple filaments 120 of the filter valve are preferably braided and can move relative to each other between their ends. The filaments are spring biased (i.e., they have "shape memory") to assume a desired crossing angle relative to each other so that the valve can self-assume a desired shape.

In the device shown in FIG. 3, the assumed shape of the filter valve occluder 110 in substantially bulb-shaped, with a larger proximal end and a smaller distal end. The shape of the occluder 110 is defined by a taper toward its distal end where it is coupled to the catheter, and a proximal inversion leading to a distal facing proximal end where it is coupled the catheter.

More particularly, the filaments or strands 120 each include a proximal portion 122, a central portion 124, and a distal portion 126. The distal portions 126 are attached circumferentially about an outer surface of the catheter 102 at a first location 128 toward the distal end but proximal of the orifice 112 of the catheter. The central portions 124 extend proximal and radially outward from the distal portions 126. The proximal portions 122 of the strands are inverted back radially from the central portions 124 to within the central portions 124, extend distally back onto the outer surface of the catheter, and are coupled circumferentially about the outer surface of the catheter 108 at a second location 130 proximally displaced from the first location 128. The proximal and distal attachment locations 128, 130 are preferably fixed to the outer surface of the catheter, for example by melt bonding or with a bonding agent; alternatively, one or both may be movable couplings, for example via a catheter mounted collar. As described in more detail below, the proximal and central portions 122, 124 of the strands are coated in a polymeric filter or membrane material 132 that extends between and across the strands 120 to render that area of the microvalve fluid-impermeable, whereas the distal portions 126 of the strands 120 are substantially uncoated in a polymeric filter such that fluid can pass between the spaces 134 of the open strands from outside the filter valve occluder to an interior 136 of the filter valve occluder 110.

Referring back to FIG. 2, an introducer sleeve (or outer catheter) 140 is optionally provided for retaining the filter valve occluder 110 in a collapsed configuration during advancement of the infusion catheter 102 with occluder 110 to the target location within the patient. When the introducer sleeve 140 is retracted from over the filter valve occluder 110 at the target location, the filter valve occluder 110 expands outward and is adapted for limited dynamically movement (radial expansion and contraction) in response to local fluid pressure conditions about the proximal and distal portions of the filter valve occluder. Alternatively, the system can be tracked to the target location without the sleeve 140.

Now, as discussed in previously incorporated U.S. Pat. No. 8,696,698, three parameters help define the performance and nature of the deployed filter valve occluder 110: the radial (outward) force of the filter valve occluder, the time constant over which the filter valve occluder changes condition from closed to open, and the pore size (if any) of the filter valve occluder.

In a preferred embodiment, the filter valve occluder 110 expands into the deployed configuration when the filter valve occluder is advanced in the vessel. Once deployed, the filter valve fully expands to the vessel wall (i.e., reaches an open condition) when the pressure at the distal orifice of the catheter 108 is greater than the blood pressure. The filter valve occluder is also in a deployed but closed condition (with filter valve occluder retracted from the vessel wall) when blood is flowing with sufficient force in a proximal to distal direction, with pressure greater than the pressure at the catheter orifice. In addition, when the radial force of expansion on the filter valve occluder (i.e., the expansion force of the filter valve occluder itself in addition to the force of pressure in the distal vessel over the distal surface area of the filter valve occluder) is greater than the radial force of compression on the filter valve occluder (i.e., force of pressure in the proximal vessel over the proximal surface area of the filter valve occluder), the filter valve occluder fully expands so that the filter valve occluder assumes the open configuration. Thus, the radial force of expansion of the filter valve occluder can be chosen to be low (as described in more detail below) so that normal blood flow in the downstream distal direction will prevent the deployed filter valve occluder from reaching the open condition, or can be chosen to be sufficiently higher so that the filter valve occluder generally remains fully open in normal blood flow.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0} K_2 = \frac{2\cos^2\beta_0}{D_0} K_3 = \frac{D_0}{\cos\beta_0}$$

and I and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), stent diameter ($D_0$), and number of filaments (n) impact the radial force of the braided valve.

In one exemplar embodiment, the filter valve occluder 110 is composed of twenty-four polyethylene terephthalate (PET) filaments 120, each having a diameter of 0.1 mm and pre-formed to an 8 mm diameter mandrel and a braid angle of 130° (i.e., the filaments are spring-biased or have a shape memory to assume an angle of 130° relative to each other when the valve assumes a fully deployed state and opens in a frustoconical configuration). The filaments 120 preferably have a Young's modulus greater than 200 MPa, and the filter valve occluder 110 preferably has a radial force of less than 40 mN in the fully deployed position (i.e., where the filaments assume their shape memory). More preferably, the filter valve occluder 110 has a radial force in the fully deployed position of less than 20 mN, and even more preferably the filter valve has a radial force of approximately 10 mN (where the term "approximately" as used herein is defined to mean±20%) in the deployed position.

In one embodiment, when subject to an infusion pressure at the distal orifice 112 of the catheter, the filter valve occluder 110 moves between deployed positions allowing downstream fluid passage (closed) and preventing fluid passage (open) in a static fluid glycerin) having a viscosity approximately equal to the viscosity of blood (i.e., approximately 3.2 cP) in 0.067 second. For purposes herein, the time it takes to move from the closed position to the open position in a static fluid is called the "time constant". According to another aspect of the invention, the filter valve 110 is arranged such that the time constant of the filter valve occluder 110 in a fluid having the viscosity of blood is between 0.01 seconds and 1.00 seconds. More preferably, the filter valve occluder 110 is arranged such that the time constant of the filter valve in a fluid having the viscosity of blood is between 0.05 and 0.50 seconds. The time constant of the filter valve occluder 110 may be adjusted by changing one or more of the parameters described above (e.g., the number of filaments, the modulus of elasticity of the filaments, the diameter of the filaments, etc.).

According to one aspect of the invention, the deployed filter valve opens and closes sufficiently quickly to achieve high capture efficiency of therapeutic agents in the presence of rapidly changing pressure conditions. More particularly, when pressure at the distal orifice 112 increases higher than the pressure in the blood vessel, the seal between the periphery of the filter valve and the vessel wall is increased, thus blocking refluxing therapeutics. It is important to note that pressure is communicated throughout the vasculature at the speed of sound in blood (1540 m/s) and that the valve opens and closes in in response to pressure changes within the blood vessel. Since the expandable filter valve responds to pressure changes, it reacts far faster than the flow rates of embolics in the blood (0.1 m/s) thereby preventing reflux of any embolics.

As will be appreciated by those skilled in the art, the braid geometry and material properties of the filaments 120 are intimately related to the radial force and time constant of the filter valve. Since, according to one aspect of the invention, the filter valve is useful in a variety of vessels of different diameters and flow conditions, each implementation can have a unique optimization. By way of example only, in one embodiment, the filter valve occluder 110 has ten filaments 120, whereas in another embodiment, the filter valve has forty filaments 120. Any suitable number of filaments can be used. Preferably, the diameter of the filaments are chosen in the range of 0.025 mm to 0.127 mm, although other diameters may be utilized. Preferably, the pitch angle (i.e., the crossing angle assumed by the braided filaments in the fully open deployed position) is chosen in the range of 100° to 150°, although other pitch angles may be used.

The proximal and central portions of the braid of the filter valve occluder 110 have a polymer coating. The polymer can be coated onto the braid by several methods, including by spraying, spinning, electrospinning, bonding with an adhesive, thermally fusing, mechanically capturing the braid, melt bonding, dip-coating, or any other desired method, to form a filter. The filter can either be a material with pores such as ePTFE, a solid material that has pores added such as polyurethane with laser drilled holes, or the filter can be a web of very thin filaments that are laid onto the braid.

Where the polymer filter 132 is a web of thin filaments, the characteristic pore size of the filter can be determined by attempting to pass beads of different diameters through the filter and finding which diameter beads are capable of passing through the filter in large quantities. The very thin filaments can be spun onto a rotating mandrel according to U.S. Pat. No. 4,738,740 with the aid of an electrostatic field or in the absence of an electrostatic field or both. The filter thus formed can be adhered to the braid structure with an adhesive or the braid can be placed on the mandrel and the filter spun over it, or under it, or both over and under the braid to essentially capture it. The filter can have some pores formed from spraying or electrospinning and then a secondary step where pores are laser drilled or formed by a secondary operation. In one embodiment a material capable of being electrostatically deposited or spun is used to form a filter on the braid, with the preferred material being capable of bonding to itself. The filter may be made of polyurethane, thermoplastic urethanes such Pellethane®, polyolefin, polyester, fluoropolymers, acrylic polymers, acrylates, polycarbonates, or other suitable material. The polymer is spun onto the braid in a wet state, and therefore it is desirable that the polymer be soluble in a solvent. In one embodiment, the filter is formed from polyurethane in a dimethylacetamide (DMA) and tetrahydrofuran (THF) solution. The polymer in solution is spun, with a preferred concentration of 5-10% solids for an electrostatic spin process and 15-25% solids for a wet spin process.

As another alternative construct for polymer-coating 132 the braid, the braid can be dip-coated to form a filter onto the braid. The braid is mounted on a mandrel having the same outer diameter as the inner diameter of the fully expanded braid. The mandrel is preferably polytetrafluoroethylene (PTFE)-coated steel, in which the PTFE acts as a release surface. Alternatively, a non-coated mandrel may be used. It is important that inner diameter of the braid and the outer diameter of the mandrel not be spaced from each other when the braid is mounted on the mandrel. Thus, they preferably have a common diameter within a tolerance of ±0.065 min. Keeping the entire inner braid in contact with the mandrel allows for the filaments to be evenly coated with the polymer, as subsequently described, so that the filter valve expands uniformly after the polymer dries. Alternately, the braid can be mounted on an oversized mandrel (greater than the inner diameter of the braid), but such will result in an increase in the braid angle of the filaments, and thereby resize the filter valve and effect the expansion force thereof. In an alternate arrangement the braid may be mounted within a tubular mandrel having the same size as the outer diameter of the braid, provided with like tolerances described above. As yet another alternative, the braid can be mounted inside an undersized tubular mandrel (having an inner diameter smaller than the outer diameter of the braid), but such will result in a decrease in the braid angle of the filaments, and thereby also resize the filter valve and effect the expansion force thereof. The type of mandrel (solid or tubular), and the location of the braid thereon (external or internal), will affect localization of the polymer on the braid (providing a smooth internally coated filter valve for external mounting on a solid mandrel and providing a smooth externally coated filter valve for internally mounting within a tubular mandrel), and thereby alter areas of lubricity for the resulting filter valve.

Once the braid is tightly mounted on (or within) the mandrel, the braid is dip coated into a polymer solution at a controlled steady rate. The solution is an elastomeric thermoplastic polymer dissolved in a solvent system with a boiling point ranging from 30-200° C. to produce a solution with a dynamic viscosity range of 50-10,000 cP. The rate of decent and accent is inversely dependent upon the viscosity of the solution and ranges from 1-100 mm/sec. The rate is critical to provide an even coating of the polymer on the braid, to allow wetting of all surfaces of the braid even at locations where the braid filaments are in contact with the mandrel and consequent wicking of the polymer coating into the braid particularly to the surface in contact with the mandrel, and to release air bubbles that may be trapped during the dipping process. By way of example, in one embodiment of the method for dipping into a thermoplastic urethane solution (Pellethane® dissolved in the solvents dimethylacetamide (DMA) and tetrahydrofuran (THF)), the rate is such that the dwell time of a 135 mm (6 inch) braid is 16 seconds. The rate is also preferably such that the polymer wicks down the length of the entire braid during withdrawal of the braid from the solution. The braid is dipped one time only into the solution to limit the thickness of the coating and thereby prevent restraint on the braid filaments and/or control smoothness of the polymer coating membrane. The controlled rate may be controlled by coupling the mandrel to a mechanized apparatus that dips and raises the braid on the mandrel at the steady and controlled rate into the polymer solution.

After the braid is withdrawn from the polymer solution, the solvent is evaporated over a time frame relative and temperature range corresponding to the solvent boiling point, with higher temperatures and longer durations utilized for high boiling point solvents. All preferred polymer solutions use some DMA to control the uniformity of the coating thickness, and may use THF to control the rate of solvent evaporation. The ratio of high boiling point solvents such as DMA to low boiling point solvents such as THF allows for control over the rate of transition from a lower viscosity high solvent content polymer solution to a high viscosity low solvent content polymer solution to a solid solvent free material, affecting the quality of the polymer membrane. In one method, the solvents are released in an oven heated to a temperature above the boiling point of DMA (165° C.) in order to rapidly release the DMA. A preferred time of heating at this temperature is 5 minutes which is sufficient to release the DMA. It is appreciated that THF has a substantially lower boiling point (66° C.) and will vaporize quickly without such substantial heating. Alternatively, the polymer-coated braid can be oven heated at a temperature below the boiling point of DMA, e.g., 80° C.-100° C., which will release the DMA from the coated braid, but at a slower rate than would occur above the boiling point of DMA. This temperature rapidly drives off the DMA while maintaining the integrity of the coated braid. A preferred time of heating at this temperature is 10 minutes which is sufficient to release the DMA. As yet another alternative, the polymer-coated braid can be allowed to dry ambient room temperature, which results in DMA release occurring at a slower rate than each of the above.

After the solvents have been released from the polymer-coated braid, the coated braid is cooled below a glass transition temperature of the polymer on the braid. Once cooled, the coated braid is released from the mandrel. If the mandrel is coated with PTFE, the braid may self-release from the mandrel or may be readily released. If the mandrel is uncoated, a release agent such as isopropyl alcohol (IPA) may be used to facilitate removal of the coated braid from the mandrel. The resulting elastomeric membrane filter formed on the braid may be elastically deformed over a range of 100-1000% elongation. In addition to Pellethane®, the membrane may be formed from, but not limited to, other polyether-based aromatic thermoplastic urethanes, polyether-based aliphatic thermoplastic urethanes (e.g., Tecoflex®), polyether block amides (e.g., Pebax®), styrene-isoprene-butadiene-styrene (SIBS), silicone, and other polymers. These polymers may be dissolved in appropriate solvents or heated to their melting point to form a fluid.

Depending on the polymer and coating technique, the coating can be fluid impermeable or porous. If porous, the coating can have a characteristic pore size between 10 μm and 500 μm, or more preferably between 15 μm and 100 μm, or even more preferably, less than 40 μm and yet more preferably between 20 μm and 40 μm. The filter valve can be adapted to allow the reflux of a contrast agent through the open filter valve as an indicator of a clinical endpoint while preventing the reflux of the therapeutic agent at the same time. In addition, by allowing blood to flow back through the filter material, even at a relatively slow rate, backpressure on the distal side of the valve can be alleviated, where such may be a desirable feature.

In yet other embodiments, the coating on the braid of filaments can be non-polymeric and applied by a suitable method. By way of example, the coating may include a metallic mesh. By way of another example, the coating may comprise a biological tissue material. Such coating materials are constructed when applied to the braid of filaments to form a barrier to passage of a therapeutic agent on the constructed occluder.

The filter valve occluder 110 is also preferably provided with a hydrophilic coating, hydrophobic coating, or other coating that affects how proteins within blood adhere to the filter. More specifically, the coating is resistant to adhesion of blood proteins. Suitable coatings include ANTI-FOG COATING 7-TS-13 from Hydromer, Inc. of Branchburg, NJ, and SERENE COATING from Surmodics, Inc, of Eden Prairie, MN. These and other coatings can be applied to the filter by, e.g., dipping, spraying, or roll or flow coating.

The filter valve occluder 110 provides several advantages over prior vessel occluders. First, the shape naturally defines a tapered lead end for advancement within the vessel. This tapered shape has significantly lower drag when advancing within the vessel and in contact with the vessel wall, thus reducing possibility of vessel spasm. Second, the shape provides a large bulbous proximal end with significantly higher resistance to antegrade flow about the flow than prior dynamic microvalve devices. This results in a greater vascular flow reduction about the valve and a significant pressure drop distal of the valve which is advantageous for various therapeutic delivery procedures. For example, for therapeutic regional delivery to various tumors in an organ, including by way of example in the liver and pancreas, it is desirable to reduce vascular flow into the organ prior to and during pressurized delivery of the therapeutic agent into the organ. In addition, the filter valve occluder has the advantages of a dynamic valve that can dynamically react to pressure changes about the proximal and distal sides of the occluder to change shape, regulate downstream pressure, and dynamically prevent reflux.

Figure 4:
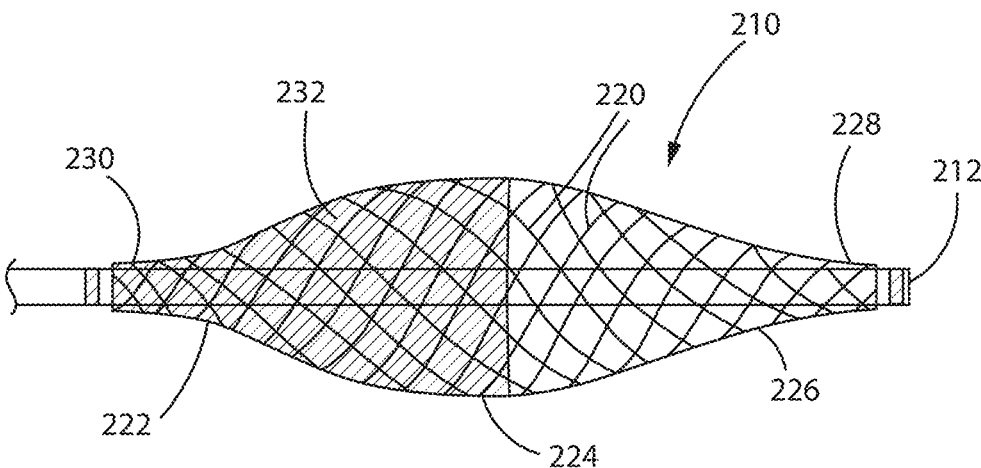
FIG. 4 is an enlarged view of a distal end of another microvalve infusion system.

Turning now to FIG. 4, in another embodiment of a filter valve occluder 210 constructed from a multistrand, elastic filament, tubular braided construction as described above (in which like parts have reference numerals incremented by 100), the distal ends 226 of the braided strands 220 are attached circumferentially about at an outer surface of the catheter 212 at a first location 228 toward the distal end but proximal of the orifice 212 of the catheter, the central portions 224 of the braided strands 220 extend proximal and radially outward from the first location 228, and the proximal portions 222 of the braided strands extend radially inward and are coupled circumferentially about the outer surface of the catheter at a second location 230 proximally displaced from the first location 228 such that the braided strands define a bulb shape. The length between the first and second locations 228, 230 is preferably fixed; however one of the first and second locations 228, 230 can be a collar movable about the outer surface of the catheter. The proximal and central portions 222, 224 of the strands are coated in a polymeric filter or membrane material 232 that extends between and across the braided strands to render that area of the microvalve fluid-impermeable, whereas the distal portions 226 of the braided strands are substantially uncoated in a polymeric filter such that fluid can pass between the open braided strands. This construct provides lower flow resistance relative to the tapered lead, bulbous proximal end construction described above, and higher drag when advancing the microvalve in the vessel.

In the embodiments described herein, the components of the filter valve occluder may be coated to reduce friction in deployment and retraction. The components may also be coated to further reduce vascular spasms, reduce thrombus formation along the valve, or to be compatible with therapeutics, biologics, or embolics. The components may be coated to increase binding of embolization agents so that they are removed from the vessel during withdrawal of the therapeutic treatment device.

In addition, the catheter and braided mesh may be separately labeled for easy visualization under fluoroscopy. The catheter can be labeled by use of any means known in the art; for example, compounding a radio-opaque material into the catheter tubing. The radio-opaque material can be barium sulfate, bismuth subcarbonate or other material. Alternatively or additionally, radio-opaque medium can be compounded into the materials of the braid and the filter. Or, as previously described, one or more of the filament strands may be chosen to be made of a radio-opaque material such as platinum iridium.

In each of the embodiments, the catheter may be a single lumen or a multi-lumen catheter. Preferably, the catheter has at least one lumen used to deliver the therapeutic agent, and one or more additional lumen may be provided, if desired, for passage of a guidewire or other devices or to administer fluids, e.g., for flushing the vessel after the administration of therapeutic agent.

The above apparatus and methods have been primarily directed to a therapeutic device which permits proximal and distal flow of biological fluid (e.g., blood) within a body vessel, and which prevents reflux of an infused therapeutic past the valve in a proximal direction. In addition, in embodiments, the configuration of the microvalve occluder is optimized to reduce blood flow past the occluder in the proximal to distal direction. The configured microvalve can also be tuned to adjust the radial force of the occluder and further reduced blow flow within the vessel. For example, in any of the embodiments, the radial force of the filter valve can be tuned by adjusting the braid angle. Tuning the radial force allows the blood flow to be reduced by up to more than 50 percent. By way of example, providing a braid angle greater than 130° will significantly reduce blood flow past the valve in the distal direction, with a braid angle of approximately 150° slowing the blood flow by 50 to 60 percent. Other braid angles can provide different reductions in distal blood flow.

While the above description has been primarily directed to use of the device for infusing a therapeutic agent, it is appreciated that the device has functionality even when delivery of a therapeutic agent is not the primary function.

There have been described and illustrated herein embodiments of devices and methods for reducing or preventing reflux of therapeutic agents in a vessel. While particular embodiments of the invention have been described, it is not intended that the invention be limited thereto, as it is intended that the invention be as broad in scope as the art will allow and that the specification be read likewise. Thus, while various materials have been listed for the microvalve filaments, the valve coating, and the catheter, it will be appreciated that other materials can be utilized for each of them in each of the various embodiments in combination and without limitation. Also, while infusion of a therapeutic agent has been referred to herein throughout, a therapeutic agent should be considered broadly including any treatment agent, including, not by limitation, drugs that target cancer cells and immunotherapy agents, including immunomodulators, vaccines, modified cells and check-point inhibitors, as well as agents aiding in the delivery of treatment agents, including but not limited to contrast agents. Also, while the invention has been described with respect to particular arteries of humans, it will be appreciated that the invention can have application to any blood vessel and other vessels, including ducts, of humans and animals. In particular, the apparatus can also be used in treatments of tumors, such as liver, renal or pancreatic carcinomas. Further, the embodiments have been described with respect to their distal ends because their proximal ends can take any of various forms, including forms well known in the art. It will therefore be appreciated by those skilled in the art that yet other modifications could be made to the provided invention without deviating from its scope as claimed.

What is claimed is:

1. A therapeutic device for delivery of a therapeutic agent within a vessel of a patient during a vascular procedure, the vessel having a vessel wall, comprising:

a) a flexible catheter sized for introduction into the vessel, the catheter having a proximal end and a distal end, an outer surface, a lumen extending between the proximal and distal ends and opening at a distal orifice; and b) a filamentary construct mounted on the outer surface of the catheter adjacent the distal end of the catheter, the construct comprising, i) a plurality of elastic filamentary strands in a tubular braid extending from a proximal end to a distal end, the plurality of elastic filamentary strands having proximal portions, central portions, and distal portions, the distal portions extend from the central portions distally and taper to the distal end of the tubular braid, the distal end longitudinally fixed to the outer surface of the catheter at a first location proximal of the distal orifice, the central portions extending proximally from the distal portions and biased to extend radially outward from the outer surface of the catheter, and the proximal portions inverting relative to the central portions to extend distally and radially inward onto the outer surface, and coupled circumferentially about the outer surface of the catheter at a second location proximally displaced from the first location, and ii) a material provided onto the proximal portions of the plurality of elastic filamentary strands and at least a portion of the central portions of the plurality of elastic filamentary strands, the material forming a barrier to passage of the therapeutic agent.

2. The therapeutic device of claim 1, wherein the proximal portions of the plurality of elastic filamentary strands are longitudinally fixed to the second location.

3. The therapeutic device of claim 1, wherein the plurality of elastic filamentary strands are independently movable relative to each other between the proximal and distal ends of the tubular braid.

4. The therapeutic device of claim 1, wherein the plurality of elastic filamentary strands comprise a nickel titanium alloy.

5. The therapeutic device of claim 1, wherein the material comprises a polymeric material.

6. The therapeutic device of claim 5, wherein the polymeric material comprises a fluid impermeable membrane.

7. The therapeutic device of claim 5, wherein the polymeric material extends between and across the plurality of elastic filamentary strands.

8. The therapeutic device of claim 5, wherein the polymeric material comprises an elastomeric polymer.

9. The therapeutic device of claim 8, wherein the elastomeric polymer comprises a thermoplastic urethane.

10. The therapeutic device of claim 8, wherein the elastomeric polymer is a silicone.

11. The therapeutic device of claim 1, wherein the filamentary construct defines spaces between the distal portions of the plurality of elastic filamentary strands for fluid communication into an interior of the filamentary construct.

12. A therapeutic device for delivery of a therapeutic agent within a vessel of a patient during a vascular procedure, the vessel having a vessel wall, comprising:

a) a flexible catheter sized for introduction into the vessel, the catheter having a proximal end and a distal end, an outer surface, a lumen extending between the proximal and distal ends and opening at a distal orifice; and b) a filamentary construct mounted on the outer surface of the catheter adjacent the distal end of the catheter, the construct comprising, i) a plurality of elastic filamentary strands in a tubular braid extending from a proximal end to a distal end, the plurality of elastic filamentary strands having proximal portions, central portions, and distal portions, the distal portions extend distally from the central portions and taper to the distal end of the tubular braid, the distal end longitudinally fixed to the outer surface of the catheter at a first location proximal of the distal orifice, the proximal portions inverting relative to the central portions to extend distally to a second location on the outer surface proximal of the first location, the proximal end longitudinally fixed to the outer surface of the catheter at the second location, and the central portions extending radially from the catheter; and ii) a fluid impermeable material provided onto at least the proximal portions of the plurality of elastic filamentary strands and at least a portion of the central portions of the plurality of elastic filamentary strands, the fluid impermeable material forming a barrier to passage of the therapeutic agent.

13. The therapeutic device of claim 12, wherein the plurality of elastic filamentary strands are independently movable relative to each other between the proximal and distal ends of the tubular braid.

14. The therapeutic device of claim 12, wherein the plurality of elastic filamentary strands comprise a nickel titanium alloy.

15. The therapeutic device of claim 12, wherein the fluid impermeable material comprises a polymeric material.

16. The therapeutic device of claim 15, wherein the polymeric material comprises a membrane.

17. The therapeutic device of claim 15, wherein the polymeric material extends between and across the plurality of elastic filamentary strands.

18. The therapeutic device of claim 15, wherein the polymeric material comprises an elastomeric polymer.

19. The therapeutic device of claim 18, wherein the elastomeric polymer comprises a thermoplastic urethane.

20. The therapeutic device of claim 18, wherein the elastomeric polymer is a silicone.

21. The therapeutic device of claim 12, wherein the filamentary construct defines spaces between the distal portions of the plurality of elastic filamentary strands for fluid communication into an interior of the filamentary construct.

* * * * *